United States Patent [19]
Mansfield

[11] Patent Number: 5,994,057
[45] Date of Patent: Nov. 30, 1999

[54] METHOD OF DETECTING ANEUPLOIDY BY AMPLIFIED SHORT-TANDEM REPEATS

[75] Inventor: Elaine S. Mansfield, Sunnyvale, Calif.

[73] Assignee: The Perkin-Elmer Corporation, Foster City, Calif.

[21] Appl. No.: 08/199,722

[22] Filed: Feb. 22, 1994

Related U.S. Application Data

[63] Continuation of application No. 07/922,444, Jul. 30, 1992, abandoned.

[51] Int. Cl.$^6$ ..................................................... C12Q 1/68
[52] U.S. Cl. .......................... 435/6; 536/24.3; 536/24.31; 536/24.33
[58] Field of Search ................................. 435/6; 536/24.3, 536/24.31, 24.33

[56] References Cited

PUBLICATIONS

Bernstein et al., J. Clin. Investigation, 83(4):1390–99, Apr. 1989.
Mutter et al. Nucleic Acids Research, 19 (15): 4203–4207 (1991) Molecular diagnosis of sex chromosome aneuploidy using quantitative PCR.
Sharma et al., Human Molecular Genetics 1(1):67.
Stratagene 1988 Catalog, p. 39.
McBride et al., in "Polymerase Chain Reaction," ed by Erlich et al. Cold Spring Harbor Laboratory Press p. 211–216, 1989.
Levanon et al., EMBO 4(1):77–84, 1985.

*Primary Examiner*—Scott W. Houtteman
*Attorney, Agent, or Firm*—Scott R. Bortner

[57] ABSTRACT

A method is provided for determining aneuploidy of selected chromosomes. An important feature of the invention is the quantitative amplification of STR markers with repeat units of at least 3 nucleotides. The amplified STR DNA is separated by size and the respective quantities of the amplified components are determined and related to chromosome copy number. The highly polymorphic nature of the STR markers permits a more sensitive and reliable quantitative analysis of the amplified DNA.

25 Claims, 4 Drawing Sheets

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

GTGAGTCAAT TCCCCAAG                                                    18

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GTTGTATTAG TCAATGTTCT CC                                               22

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GCACTTCAGA CACCACCTCC AACAAC                                           26

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GCTGTTTGCA AACCTGATGC TGTCAC                                           26

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CCGTACCATC TACCTGGCCT GCCTAACGA                                        29

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CGGGTAGCTC AGAGTCCAGG CACACGCGG                                        29

METHOD OF DETECTING ANEUPLOIDY BY AMPLIFIED SHORT-TANDEM REPEATS

This application is a continuation of application Ser. No. 07/922,444 filed on Jul. 30, 1992 now abandoned.

The present invention relates generally to a method of diagnosing genetic anomalies associated with chromosomal aneuploidy, and more particularly, to a method of relating the amplified products of chromosome-specific short terminal repeat loci to chromosomal aneuploidy and gene duplication.

BACKGROUND

Chromosomal aneuploidy is associated with a large number of genetic disorders that could be prevented or prepared for by appropriate diagnosis, e.g. Verp et al, chapter 7, in Filkins and Russo, Eds., Human Prenatal Diagnosis (1990). Such disorders include Down's syndrome associated with chromosome 21 trisomy, Edward's syndrome associated with chromosome 18 trisomy, Plateau's syndrome associated with chromosome 13 trisomy, Turner's syndrome associated with an absence of an X chromosome (XO), Kleinfelter's syndrome associated with an extra X chromosome (XXY), XYY syndrome, triple X syndrome, and the like. Presently, of the 15,600 annual births in the United States with chromosomal abnormalities (and 643,000 worldwide), 53% have sex chromosome aneuploidies, 26% have autosomal trisomies, and the remaining have autosomal rearrangements. There is a clear need for accurate, inexpensive, and convenient aneuploidy diagnostics.

A variety of diagnostic approaches have been taken or have been proposed to detect the presence of aneuploidy, e.g. construction and microscopic examination of karyotypes, flow cytometric examination of chromosomes, assay for enzymatic markers, in situ hybridization, quantitative amplification of selected chromosome-specific markers, and the like, e.g. Khan et al, European patent application No. 89300963.9. Unfortunately, most of these approaches are either technically difficult to perform, expensive, or rely on the subjective evaluation of a clinician which leads to unacceptable rates of misdiagnosis.

Recently many diagnostic and forensic assays have been proposed which are based on the amplification and detection of highly polymorphic classes of repetitive DNA that are present in the human genome, e.g. Craig et al, J. Forensic Sci., Vol. 33, pgs. 1111–1126 (1988); Edwards et al, Genomics, Vol. 12, pgs. 241–253 (1992); Boerwinkle et al, Proc. Natl. Acad. Sci., Vol. 86, pgs. 212–216 (1989); Tautz, Nucleic Acids Research, Vol. 17, pgs. 6463–6471 (1989); and the like. Typically, a segment of DNA that contains the repeated sequence is amplified by polymerase chain reaction (PCR) and then sized by denaturing polyacrylamide gel electrophoresis. In regard to this approach, the so-called "short tandem repeat" or "STR" repetitive DNA has been of particular interest for diagnostic and mapping applications because of its size and genomic distribution. The length of the repeated unit in this class of DNA is typically from 2 to 6 nucleotides, and the overall length of the tandem repeat ranges from several tens to several hundreds of nucleotides making them convenient targets for PCR amplification and electrophoretic separation.

Unfortunately, the implementation of many of these detection schemes has been complicated because of imperfections in the amplification technology. For example, where amplification products must be electrophoretically separated for an assay readout, frequently secondary bands appear adjacent to a primary band, particularly when 2-nucleotide repeat sequences are amplified. This greatly complicates the quantitative analysis of the amplified product as the secondary bands of one allele may overlap the primary band(s) of other alleles.

It would be desirable to be able to detect aneuploidy using the DNA amplification approaches without the problems caused by spurious bands appearing in the electrophoretically separated amplification products.

SUMMARY OF THE INVENTION

The invention is directed to the detection of aneuploidy by the quantitative amplification of selected short tandem repeat (STR) DNAs. An important feature of the invention is the amplification of STRs whose repeated units are at least 3 nucleotides in length. More preferably, the repeat units of the amplified STRs are from 4 to 6 bases in length and the total length of the amplified STR is from a few tens to a few hundred nucleotides. In one aspect of the invention, a method and kits are provided for simultaneously amplifying one or more chromosome-specific STRs, for separating the amplified STRs by size, and for determining the relative quantities of amplified STR DNA present. Preferably, the amplified products are separated electrophoretically.

In one preferred embodiment of the invention, a cell sample is assayed for trisomy 21 by amplifying the DNA containing the tetranucleotide STR repeat $[TCTA]_n$ at the D21S11 locus. The relative amounts of the amplified STRs are then determined after separation by gel electrophoresis.

In another preferred embodiment, a cell sample is assayed for trisomy 18 by amplifying the DNA of STRs $[ATGG]_n$ and $[TGGA]_n$ at the 5' end of the myelin basic protein gene.

In another preferred embodiment, a sample is assayed for multiple X syndrome by amplifying the DNA of STRs HUMARA$[AGC]_n$ and HUMHPRTB$[AGAT]_n$. Normal male and female DNAs can be differentiated by co-amplifying X-linked STR markers with reference markers on the Y chromosome and from an autosome. This also allows detection of various sex chromosome aneuploidies.

In yet another preferred embodiment, a sample is assayed for Lesch-Nyhan Syndrome (caused by genetic changes at the HPRT gene on the X chromosome) by amplifying the DNA of STRs HUMARA$[AGC]_n$ and HUMHPRTB$[AGAT]_n$.

As used herein, the term "aneuploidy" refers to the condition wherein cells of an individual contain an abnormal number of chromosomes. The term also encompasses the condition wherein individual genes are present in abnormal quantity, or wherein fragments of individual genes are present in abnormal quantity.

The invention permits a more reliable and sensitive diagnosis of aneuploidy and other kinds of gene or gene fragment duplication involving STRs by providing better resolved and/or less noisy electropherograms from which to estimate chromosome and/or gene copy number. The invention also permits the determination of the parental contributions to aneuploidy and of whether the aneuploidy-causing event occurred in spermatogenesis or oogenesis. The invention is based in part on the discovery that the highly polymorphic lengths of the STR loci permit a more accurate quantitation of the amplified products because of the high probability that the amplified products will have different lengths. Accordingly, the method of the invention comprehends the simultaneous amplification of one or more kinds of STR.

BRIEF DESCRIPTION OF THE FIGURES

FIG. 1 displays electropherograms of amplified chromosome 21-specific STRs from two normal individuals and two individuals with chromosome 21 trisomy. The electropherograms illustrate the four types of patterns that can be identified (triploidy or dual heterozygous for trisomy samples and heterozygous or homozygous for controls).

FIG. 2 displays electropherograms of amplified chromosome 18-specific STRs from a chromosome 18 trisomy patient and from two control samples.

FIG. 3 displays electropherograms of amplified chromosome X-specific STRs from individuals and cell lines that have various chromosome X aneuploidies.

FIG. 4 displays electropherograms of two X-linked STRs co-amplified to measure gene dosage in the HUMARA and HPRT genes. Comparison of electropherograms from a patient with a duplication of the HPRT STR leading to Lesch-Nyhan syndrome with both male and female controls provides direct quantitative confirmation of the HPRT gene anomaly leading to disease in this case.

DETAILED DESCRIPTION OF THE INVENTION

Figure 1A:
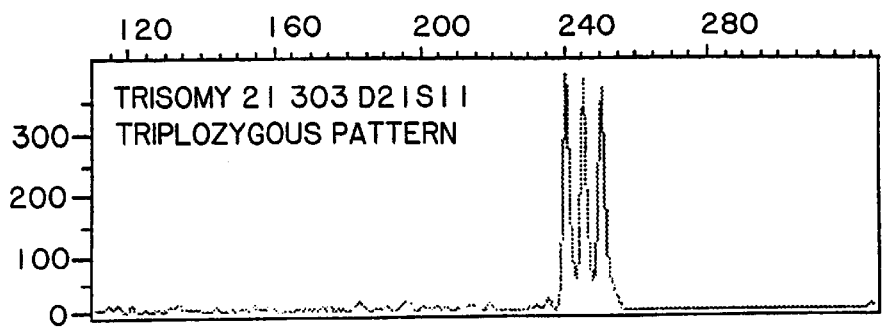
FIG. 1A displays an electropherogram of a trisomy 21 patient with a triplozygous pattern.
Figure 1B:
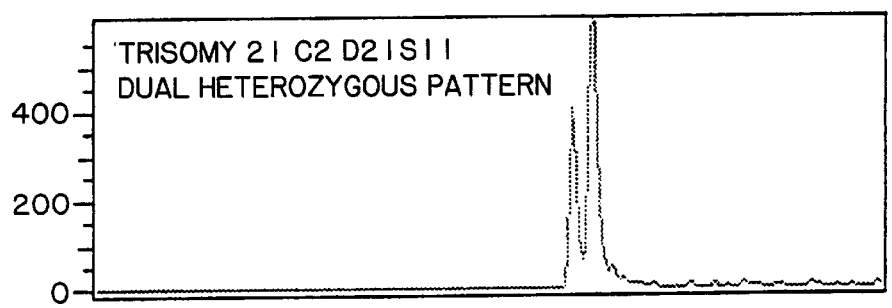
FIG. 1B displays an electropherogram of a trisomy 21 patient with a dual heterozygous pattern.
Figure 1C:
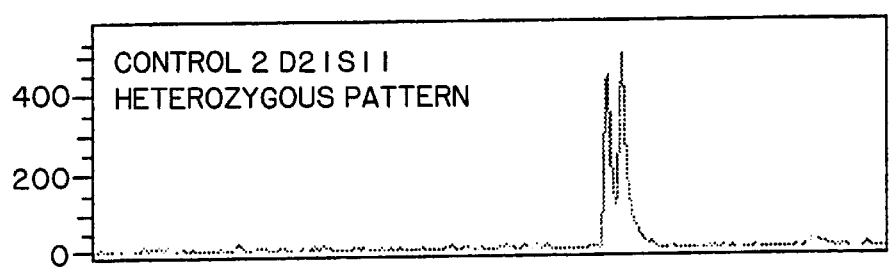
FIG. 1C displays a control electropherogram of an individual heterozygous at the D21S11 STR locus.
Figure 1D:
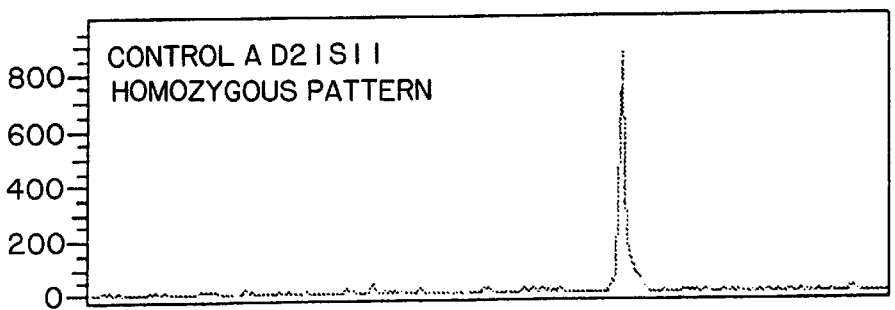
FIG. 1D displays a control electropherogram of an individual homozygous at the D21S11 STR locus.

The invention is directed to a method and kits for assaying aneuploidy of a pre-selected chromosome. The method comprises the steps of (1) simultaneously amplifying one or more chromosome-specific STRs to form an amplification mixture comprising copies of the one or more chromosome-specific STRs in concentrations substantially proportional to their respective starting concentrations, (2) separating the amplified chromosome-specific STRs from the amplification mixture according to size, and (3) determining the relative concentrations of the one or more chromosome-specific STRs.

Preferably, the STR DNA is amplified by polymerase chain reaction, a technique well known in the art and described in the following references: Mullis et al, U.S. Pat. Nos. 4,683,195; 4,800,159; 4,965,188; Mullis, U.S. Pat. No. 4,683,202; Gelfand et al, U.S. Pat. No. 4,889,818; and Innis et al, Editors, PCR Protocols (Academic Press, New York, 1990). Preferably, PCR is carried out with a commercially available thermal cycler, e.g. Perkin Elmer-Cetus. Primers for PCR amplification are readily synthesized by standard techniques, e.g. solid phase synthesis via phosphoramidite chemistry, Caruthers et al, U.S. Pat. Nos. 4,458,066; 4,415, 732; Beaucage et al, Tetrahedron, Vol. 48, pgs. 2223–2311 (1992); Applied Biosystems User Bulletin No. 13 dated Apr. 1, 1987; and the like.

Chromosome-specific STRs are selected by choosing synthesizing primers that hybridize to adjacent unique sequence regions. The unique sequence regions will ensure that only the STR specific for the desired chromosome will be amplified. Appropriate STRs may be identified from publicly available DNA sequence data bases, such as GeneBank™ or can be identified from libraries of chromosome-specific DNA libraries using the method described by Edwards et al, Am. Hum. Genet., Vol. 49, pgs. 746–756 (1991). Several factors affect the selection of primers for amplification, e.g. the relative stability of the primers when bound to target DNA-which largely depends on relative GC content, the presence or absence of secondary structures in the target DNA, relative length of primers, and the like. Guidance for selecting appropriate primers for amplifying any given STR can be found in Rychlik et al, Nucleic Acids Research, Vol. 17, pgs. 8543–8551 (1989); Lowe et al, Nucleic Acids Research, Vol. 18, pgs. 1757–1761 (1990); Hillier et al, PCR Methods and Applications, Vol. 1, pgs. 124–128 (1991); and the like. Preferably, the STRs are amplified by 20 to 35 PCR cycles. More preferably, STRs are amplified by 25 to 30 PCR cycles. As used herein, the term "PCR primers" refers to primer complementary to sequences adjacent to an STR to be amplified. Preferably, PCR primers are from 15 to 25 nucleotides long. Preferably, the PCR primers are in the range of from 0 to 1–2 hundred nucleotides of the STR to be amplified. More preferably, the PCR primers are in the range of from 0 to 50 nucleotides of the STR to be amplified.

Preferably, the amplification products, i.e. the copies of STR DNA produced in the amplification step, are labeled to facilitate their quantification after separation. A variety of different labeling approaches are suitable for use with the present invention, including the direct or indirect attachment of radioactive moieties, fluorescent moieties, electron dense moieties, and the like. It is only important that the signal generated by each copy of the target STR DNA be capable of generating a signal of the same magnitude (or at least of a known relative magnitude), so that relative quantities of amplified STR DNA can be determined. There are several means available for derivatizing oligonucleotides with reactive functionalities which permit the addition of a label. For example, several approaches are available for biotinylating an PCR primer so that fluorescent, enzymatic, or electron density labels can be attached via avidin: Broken et al, *Nucleic Acids Research*, Vol. 5, pgs. 363–384 (1978), disclose the use of ferritin-avidin-biotin labels; Chollet et al, *Nucleic Acids Research*, Vol. 13, pgs. 1529–1541 (1985), disclose biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such isothiocyanate, N-hydroxysuccinimide, or the like, e.g. Connolly, *Nucleic Acids Research*, Vol. 15, pgs. 3131–3139 (1987); Gibson et al, *Nucleic Acids Research*, Vol.15, pgs. 6455–6467 (1987); Miyoshi et al, U.S. Pat. No. 4,605,735. Methods are also available for synthesizing sulfhydryl-derivatized oligonucleotides which can be reacted with thiol-specific labels, e.g. Fung et al, U.S. Pat.

No. 4,757,141; Connolly, *Nucleic Acids Research*, Vol. 13, pgs. 4485–4502 (1985); and Spoat et al, *Nucleic Acids Research*, Vol.15, pgs. 4837–4848 10(1987). A comprehensive review of methodologies for labeling DNA fragments is provided by Matthews et al, *Anal. Biochem.*, Vol 169, pgs. 1–25 (1988).

Preferably, amplified STR DNA is labeled fluorescently by linking a fluorescent molecule to one or more primers as taught by Fung et al, U.S. Pat. Nos. 4,757,141; 4,855,225; or the like, which are incorporated by reference. Preferably, copies of different STRs are labeled with different fluorescent labels to facilitate quantitation. Guidance for selecting appropriate fluorescent labels can be found in Smith et al, Methods in Enzymology, Vol. 155, pgs. 260–301 (1987); Karger et al., Nucleic Acids Research, Vol. 19, pgs. 4955–4962 (1991); Haugland, Handbook of Fluorescent Probes and Research Chemicals (Molecular Probes, Inc., Eugene, 1989), and the like. Preferred fluorescent labels include, fluorescein and derivatives thereof, such as disclosed by Khanna et al, U.S. Pat. No. 4,318,846 and/or Lee et al, Cytometry, Vol. 10, pgs. 151–164 (1989), tetramethylrhodamine, rhodamine X, Texas Red, and the like. Most preferably, when a plurality of fluorescent dyes are employed they are spectrally resolvable, as taught by Fung et al (cited above). Briefly, as used herein "spectrally resolvable" fluorescent dyes are those with quantum yields, emission bandwidths, and emission maxima that permit electrophoretically separated polynucleotides labeled thereby to be readily detected despite substantial overlap of the concentration bands of the separated polynucleotides.

PCR primers of the invention can also be radioactively labeled with 32p using standard protocols, e.g. Maniatis et al, *Molecular Cloning: A Laboratory Manual* (Cold Spring Harbor Laboratory, New York, 1982); *Current Protocols in Molecular Biology*, Unit 6.4 (John Wiley & Sons, New York, 1987); or Maxim and Gilbert, *Meth. Enzymol.*, Vol. 65, pgs. 499–560 (1980).

An important feature of the invention is the separation of the amplified STRs from a sample by size. This may be accomplished in a variety of ways, including by filtration, high performance liquid chromatography, electrophoresis, affinity collection, e.g. Syvanen et al, Nucleic Acids Research, Vol. 16, pgs. 11327–11338 (1988), and the like. Preferably, the amplified STRs are separated from the amplified product mixture by gel electrophoresis or capillary electrophoresis. More preferably, the amplified STRs are fluorescently labeled and separated by gel electrophoresis on a instrument such as a model 362 Gene Scanner (Applied Biosystems, Foster City, Calif.), described in the following references: Mayrand et al, Clinical Chemistry, Vol. 36, pgs. 2063–2071 (1990); Mayrand et al, Annales de Biologie Clinique, Vol. 91, pgs. 224–230; and Mayrand et al, Appl. and Theoret. Electrophoresis, Vol. 3, pgs. 1–11 (1992). Accordingly, these references are incorporated by reference.

Chromosomal DNA of an individual who is being tested for aneuploidy is obtained from a cell sample from that individual. Cell samples can be obtained from a variety of tissues depending on the age and condition of the individual. Preferably, cell samples are obtain from peripheral blood using well known techniques, e.g. Kawasaki, chapter 19 in Innis et al (cited above). Preferably, in fetal testing, a sample is obtained by amniocentesis, e.g. Barter, Am. J. Obstet. Gynecol. Vol. 99, pgs. 795–805; or choronic villi sampling, e.g. Jackson, CVS Newsletter, No. 25 (March 30). Preferably, DNA is extracted from the sample using standard procedures, e.g. phenol:chloroform extraction as described by Maniatis et al, Molecular Cloning (Cold Spring Harbor, N.Y., 1982); and Higuchi, PCR Applications, May 1989, Issue 2 (Perkin Elmer-Cetus Users Bulletin). Cell samples for fetal testing can also be obtained from maternal peripheral blood using fluorescence-activated cell sorting, e.g. as described by Iverson et al, Prenatal Diagnosis, Vol. 9, pgs. 31–48 (1981).

Kits for carrying out the method of the invention include sets of labeled primers for the STR(s) to be amplified, polymerase buffer solution in which a DNA polymerase can extend the primers in the presence of deoxynucleoside triphosphates, DNA polymerase, and deoxynucleoside triphosphates. Preferably, the labeled primers include fluorescent labels and the DNA polymerase is Taq DNA polymerase. More preferably, the fluorescent labels are selected from the group consisting of fluorescein, rhodamine, and derivatives thereof, including carboxyfluorescien, 4,7-dichlorofluoresceins, tetramethylrhodamine, rhodamine X, and derivatives thereof.

EXAMPLE 1

Detection of Trisomy 21 by Quantitative Amplification of the STR $(TCTA)_n$ at the D21 S11 Locus DNA was extracted from blood samples of human donors or from lymphocyte or amniocyte cultures using a standard phenol:chloroform extraction procedure (Applied Biosystems DNA/RNA Extractor Model 340 User Bulletin No. 14, October 1987) and the 341 Nucleic Acid Extractor (Applied Biosystems, Inc.). The concentration of each DNA sample was adjusted to 50 ng/$\mu$l using half strength Tris-EDTA buffer (5 mM Tris pH 8.2 and 1 mM EDTA) in double distilled sterile water. PCR primers were end-labeled with fluorescent dyes using a previously described protocol of Gibbs et. al. 1989; Proc Natl Acad Sci 86, pp. 1919–1923. The following stock solutions were prepared and mixed together in master PCR mixes:

10(X) PCR buffer—100 mM Tris-HCl pH 8.3, 500 mM KCl, 15 mM $MgCl_2$

Primers each at 5 $\mu$M 2.5 mM dinucleotide phosphates (dATP, dCTP, dGTP, gTTP or "dNTPs")

100 mM $\beta$-mercaptoethanol

DNA - concentrations were adjusted to 50 ng/$\mu$l

PCR Primers at D21S11 locus:

JOE- 5'-gtgagtcaattccccaag-3'    (SEQ ID NO:1)

5'-gttgtattagtcaatgttctcc-3'    (SEQ ID NO:2)

"JOE" is 2',7'-dimethoxy-4',5'-dichlorofluorescein as described in Fung et al, U.S. Pat. No. 4,855,225, which is incorporated by reference.

D21 S11 PCR Amplification Conditions: The protocol of Sharama and Litt (Human Molecular Genetics 1:67 1992) was substantially modified to accommodate the increased sensitivity of multicolor fluorescent detection and automated quantitation. PCR amplification was carried out under the following conditions:

A final reaction volume of 25 $\mu$l contained 50 ng genomic DNA, 200 $\mu$M dNTPs, 0.2 $\mu$M of each PCR primer (21 S11 F and 21 S11 R), 10 mM $\beta$-mercaptoethanol and PCR buffer (10 mM Tris HCl pH 8.3, 50 mM KCl, 1.5 mM $MgCl_2$). The reaction mixture, in 80% total volume, was heated in a thermal cycler unit for 5 minutes at 80° C. under mineral oil to thoroughly denature the DNA and the allow of a "hot start" of the PCR reaction. The PCR was initiated with the addition of 2.5 units AmpliTaq—polymerase (5 μl of 1:10 dilution of stock solution supplied by the manufacturer, Perkin-Elmer Cetus, Norwalk, Conn.) and PCR carried out for 26 cycles of amplification denaturing at 94° C. for 30 seconds, annealing at 58° C. for 30 seconds and extending at 72° C. for 30 seconds. This is followed by a terminal extension at 72° C. for 10 minutes and PCR product is stored at 4° C. until analysis.

One μl of PCR product in 3.5 μl urea loading buffer (8M urea in 1× TBE buffer (89 mM Tris, 89 mM Borate, 2 mM EDTA) with 5 mg/ml blue dextran) and 0.5 μl internal lane size standard (GENESCAN-2500 ROX, Applied Biosystems, Inc.) was applied to a 24 cm 6% denaturing polyacrylamide gel (30 ml gel solution contains 14.4 g urea, 1.71 g acrylamide, 0.09 g bis-acrylamide, 180 μl freshly prepared 10% ammonia persulfate in 1× TBE buffer (89 mM Tris, 89 mM Borate, 2 mM EDTA) that was filtered prior to polymerization initiated with 15 μl TEMED). The DNA was subjected to constant current electrophoresis at 800 volts for 8 hours and data automatically analyzed using the 362 GENE SCANNER Fluorescent Fragment Analyzer. The results are shown in FIG. 1. Panel A displays an electropherogram of a trisomy 21 patient with a triplozygous pattern. That is, three different alleles of the STR at the D21 S11 locus are evident. Most trisomy patients display this pattern. Panel B displays an electropherogram of a trisomy 21 patient with a dual heterozygous pattern. That is, three STR D21 S11 alleles have been amplified, but two are the same size (242 bp). Thus, the electropherogram shows two peaks indicating a dosage ratio of 2:1. Panel C displays a control electropherogram of an individual heterozygous at the D21 S11 STR locus; thus, a 1:1 dosage ratio is evidenced. Panel D displays another control electropherogram of an individual homozygous at the D21 S11 STR locus; thus, a single peak of double dosage is evidenced (the alleles being 246 bp in length).

EXAMPLE 2

Detection of Trisomy 18 by Quantitative Amplification of the STRs $(ATGG)_{12}$ and $(TGGA)_g$ at the Myelin Basic Protein Locus (SE37)

In this example two fragments were generated for each allele amplified because the SE37R primer binds at two locations, one distal to the $(ATGG)_{12}$ STR relative to the SE37F primer and one distal to the $(TGGA)_g$ STR relative to the SE37F primer.

SE37 PCR Amplification Conditions: A final reaction volume of 25 μl contained 50 ng genomic DNA, 200 μM dNTPs, 0.4 μM of each PCR primers for 18SE37 (SE37F=FAM-5'-ggacctcgtgaattacaatc-3' where FAM is fluorescein as described in Fung et al, U.S. Pat. No. 4,855,225 and SE37R=5'-atttacctacctgttcatcc-3'), 10 mM β-mercaptoethanol and PCR buffer (10 mM Tris HCl pH 8.3, 50 mM KCl, 1.5 mM MgCl$_2$). The reaction mixture, in 80% total volume, was heated in a thermal cycler unit for 5 minutes at 80° C. under mineral oil to thoroughly denature the DNA and the allow of a "hot start" of the PCR reaction. The PCR was initiated with the addition of 2.5 units AmpliTaq polymerase (5 μl of 1:10 dilution of stock solution supplied by the manufacturer, Perkin-Elmer Cetus, Norwalk, Conn.) and PCR carried out for 28 cycles of amplification denaturing at 94° C. for 90 seconds, annealing at 55° C. for 60 seconds and extending at 72° C. for 60 seconds. This was followed by a terminal extension at 72° C. for 10 minutes and PCR product is stored at 4° C. until analysis.

Figure 2A:
FIG. 2A displays an electropherogram from a control DNA that is heterozygous for the shorter STR (ATGG) repeat and homozygous for the longer (TGGA) repeat on chromosome 18.
Figure 2B:
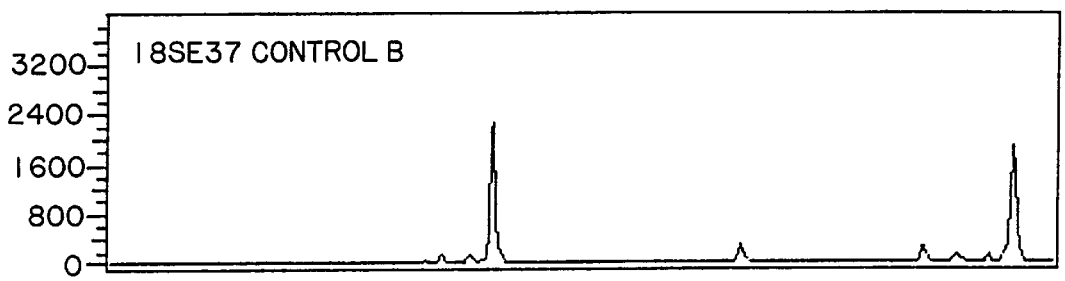
FIG. 2B displays an electropherogram from a control DNA that is homozygous at both STR repeats.
Figure 2C:
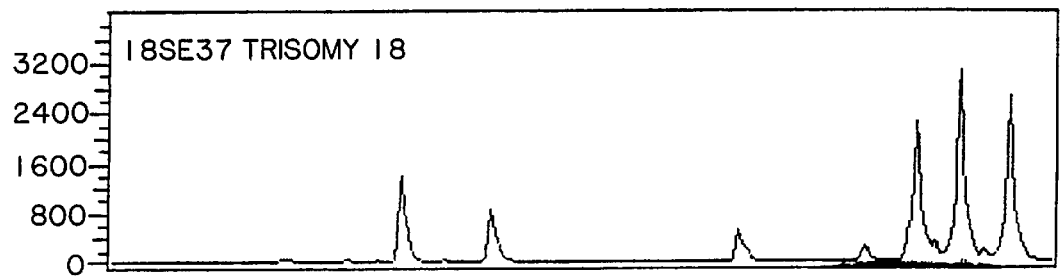
FIG. 2C displays an electropherogram from a patient with trisomy 18.
Figure 3A:
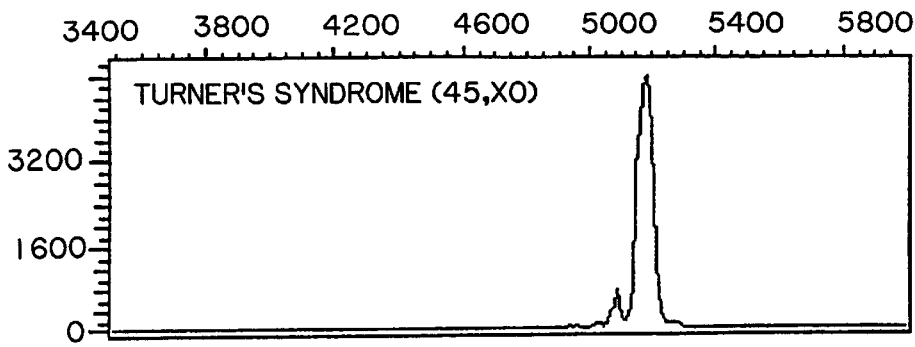
FIG. 3A displays an electropherogram of the HUMHPRTB repeat in a patient with Turner's syndrome (45,XO).
Figure 3B:
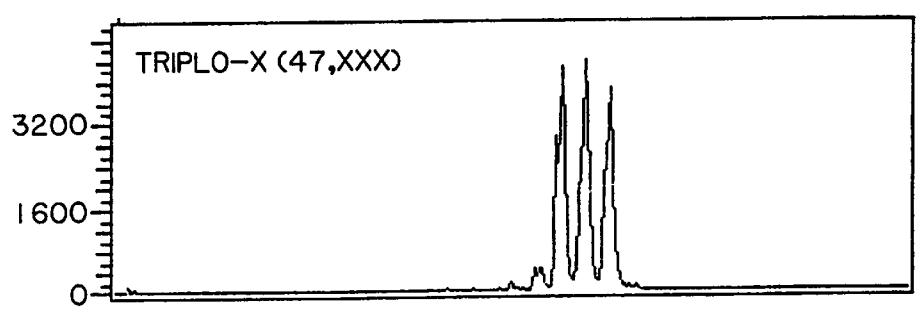
FIG. 3B displays an electropherogram of the HPRTB repeat in a patient with Triplo-X syndrome (47,XXX).
Figure 3C:
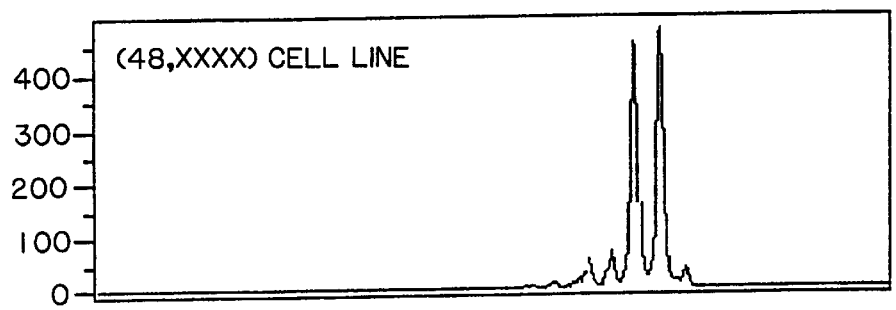
FIG. 3C displays an electropherogram of HPRTB STR amplified from a (48,XXXX) cell line, derived from a somatic tumor.
Figure 3D:
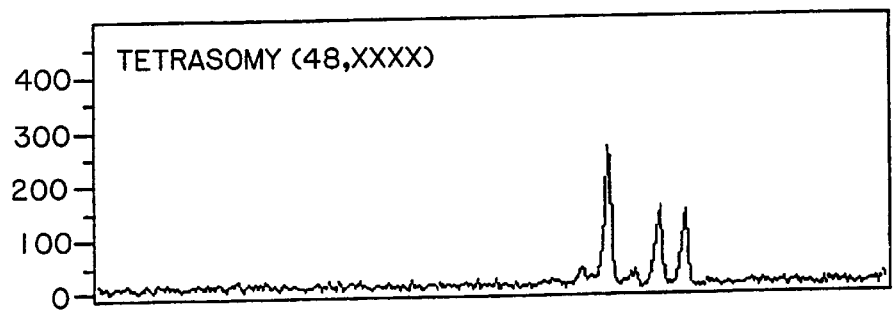
FIG. 3D displays an electropherogram of the HPRT STR from a tetrasomy (48, XXXX) patient.
Figure 3E:
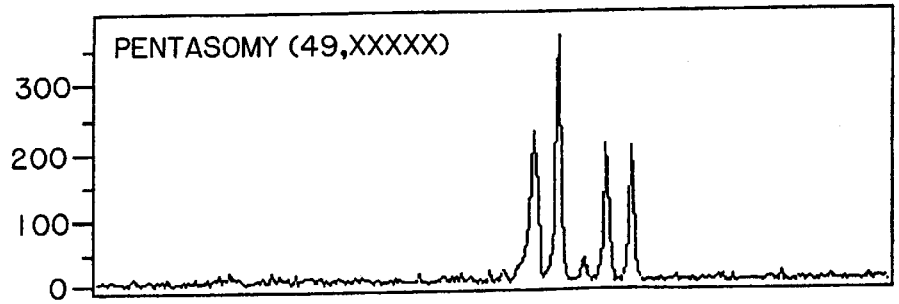
FIG. 3E displays an electropherogram of an X-linked STR in a patient with a pentasomy (49,XXXXX).
Figure 4A:
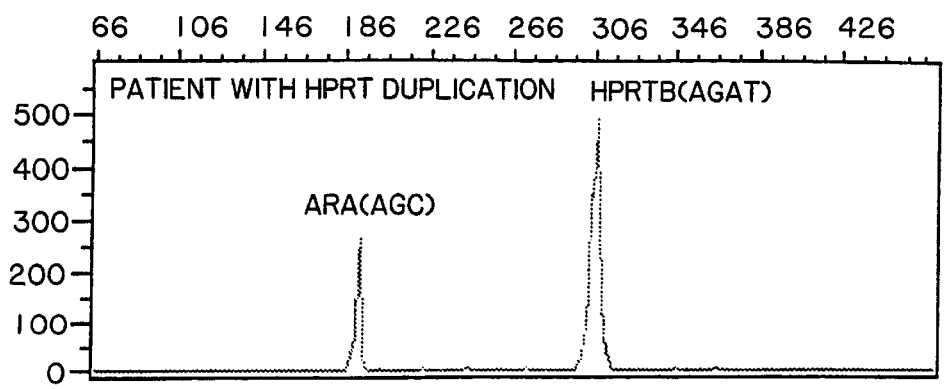
FIG. 4A displays an electropherogram of the Lesch-Nyhan patient's DNA that contains a duplication in the vicinity of the HPRTB STR.
Figure 4B:
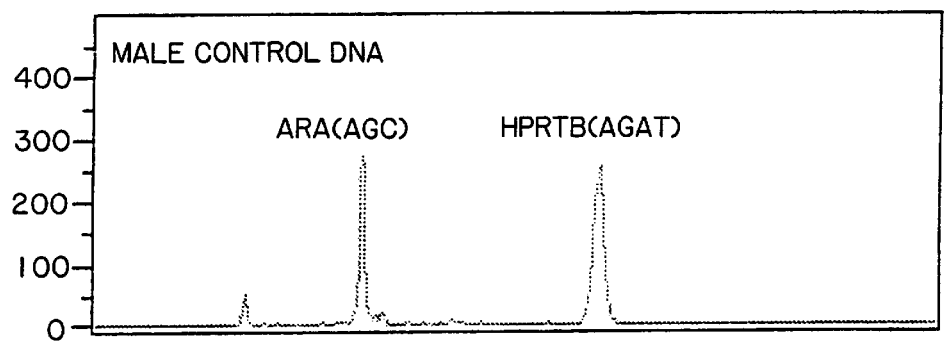
FIG. 4B displays data from a normal hemizygous male control.
Figure 4C:
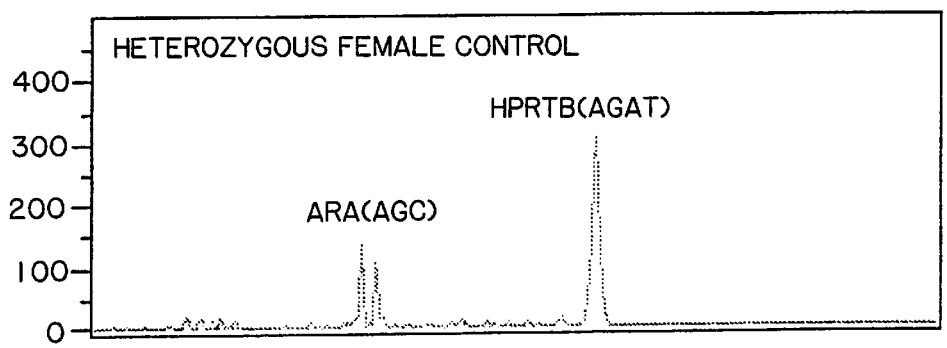
FIG. 4C displays data from a heterozygous female control.
Figure 4D:
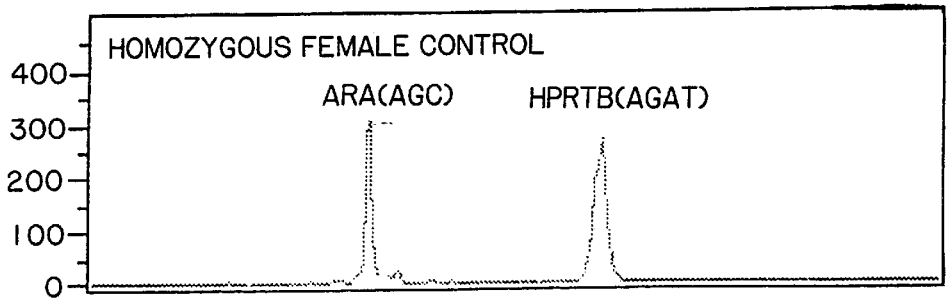
FIG. 4D displays data from a homozygous female control.

One μl of PCR product in 3.5 μl urea loading buffer (8M urea in 1× TBE buffer (89 mM Tris, 89 mM Borate, 2 mM EDTA) and 0.5 μl internal lane size standard (GENESCAN-2500 ROX, Applied Biosystems, Inc.) was applied to a 24 cm 6% denaturing polyacrylamide gel (30 ml gel solution contains 14.4 g urea, 1.71 9 acrylamide, 0.09 g bis-acrylamide, 180 μl freshly prepared 10% ammonia persulfate in 1× TBE buffer (89 mM Tris, 89 mM Borate, 2 mM EDTA) that was filtered prior to polymerization initiated with 15 μl TEMED). The DNA was subjected to constant current electrophoresis at 800 volts for 10 hours and data automatically analyzed using the 362 GENE SCANNER Fluorescent Fragment Analyzer. The results are shown in FIG. 2. Panel A displays an electropherogram from a control DNA that is heterozygous for the shorter STR (ATGG) repeat and homozygous for the longer (TGGA) repeat on chromosome 18. Panel B displays an electropherogram from a control DNA that is homozygous at both STR repeats. Panel C displays an electropherogram from a patient with trisomy 18. The shorter (ATGG) repeat in this profile is consistent with dual heterozygous type and the longer (TGGA) repeat is consistent with a triplozygous profile.

EXAMPLE 3

Detection of Multiple X Syndrome

A final reaction volume of 25 μl contained 50 ng genomic DNA, 200 μM dNTPs, 0.4 μM of each PCR primers for HPRTB (XHPRTF=FAM-5'-atgccacagataatacacatcccc-3' and XHPRTR=5'-ctctccagaatagttagatgtaggtat-3'), 0.1 μM of each PCR primers for HUMARA (XARAF=JOE-5'-tccagaatctgttccagagcgtgc-3' and XARAR=5'-gctgtgaaggttgctgttcctcat-3'), 10 mM β-mercaptoethanol and PCR buffer (10 mM Tris HCl pH 8.3, 50 mM KCl, 1.5 mM MgCl$_2$). The reaction mixture, in 80% total volume, was heated in a thermal cycler unit for 5 minutes at 80° C. under mineral oil to thoroughly denature the DNA and the allow of a "hot start" of the PCR reaction. The PCR was initiated with the addition of 2.5 units AmpliTaq polymerase (5 μl of 1:10 dilution of stock solution supplied by the manufacturer, Perkin-Elmer Cetus, Norwalk, Conn.) and PCR carried out for 25 cycles of amplification denaturing at 95° C. for 45 seconds, annealing at 60° C. for 30 seconds and extending at 72° C. for 30 seconds. This was followed by a terminal extension at 72° C. for 10 minutes and PCR product was stored at 4° C. until analysis.

One μl of PCR product in 3.5 μl urea loading buffer (8M urea in 1× TBE buffer (89 mM Tris, 89 mM Borate, 2 mM EDTA) and 0.5 μl internal lane size standard (GENESCAN-2500 ROX, Applied Biosystems, Inc.) was applied to a 24 cm 6% denaturing polyacrylamide gel (30 ml gel solution contains 14.4 9 urea, 1.71 g acrylamide, 0.09 g bis-acrylamide, 180 μl freshly prepared 10% ammonia persulfate in 1× TBE buffer (89 mM Tris, 89 mM Borate, 2 mM EDTA) that was filtered prior to polymerization initiated with 15 μl TEMED). The DNA was subjected to constant current electrophoresis at 800 volts for 10 hours and data automatically analyzed using the 362 GENE SCANNER Fluorescent Fragment Analyzer.

The following PCR primers were designed to co-amplify unique single copy genes from chromosome 1 (a reference chromosome found in all genomes) and the Y chromosome:

1STS1  FAM-5'gcacttcagacaccacctccaacaac-3'  (SEQ ID NO: 3)

1STS2  FAM-5'gctgtttgcaaacctgatgctgtcac-3'  (SEQ ID NO: 4)

Ytest1 FAM-5'ccgtaccatctacctggcctgcctaacga-3'  (SEQ ID NO: 5)

Ytest2 FAM-5'cgggtagctcagagtccaggcacacgcgg-3'  (SEQ ID NO: 6)

Primers were selected from a unique sequenced tagged site (STS) on chromosome 1 and an unidentified open reading frame on the Y-chromosome (GenBank entry HUMYTEST) for template regions. The PCR reaction amplifies a 229 bp PCR product in all samples as PCR control reference marker and a 165 bp PCR product from male DNA specific to the Y-chromosome. To accommodate the sensitivity of multicolor fluorescent detection and automated quantitation, PCR amplification was carried out under the following conditions:

A final reaction volume of 25 μl contained 50 ng genomic DNA, 200 μM dNTPs, 0.2 μM of each PCR primers (1STSF, 1STSR, Ytest1 and Ytest2), 10 mM β-mercaptoethanol and PCR buffer (10 mM Tris HCl pH 8.3, 50 mM KCl, 1.5 mM $MgCl_2$). The reaction mixture, in 80% total volume, was heated in a thermal cycler unit for 5 minutes at 80° C. under mineral oil to thoroughly denature the DNA and the allow of a "hot start" of the PCR reaction. The PCR was initiated with the addition of 2.5 units AmpliTaq—polymerase (5 μl of 1:10 dilution of stock solution supplied by the manufacturer, Perkin-Elmer Cetus, Norwalk, Conn.) and PCR carried out for 25 cycles of amplification denaturing at 95° C. for 45 seconds, annealing at 60° C. for 30 seconds and extending at 72° C. for 30 seconds. This was followed by a terminal extension at 72° C. for 10 minutes and PCR product is stored at 4° C. until analysis.

One μl of PCR product in 3.5 μl 2× loading buffer (Supplied by Applied Biosystems, Inc as described in Mayrand et. al. 1991 Annales de Biol Clinique Vol. 4, pp. 224–230.) and 0.5 μl internal lane size standard (GENESCAN-1000 ROX, Applied Biosystems, Inc.) was applied to a 24 cm 2% agarose gel (160 ml gel solution contains 3.2 g SeaPlaque Agarose (FMC, Inc. ) in 1× TBE buffer (89 mM Tris, 89 mM Borate, 2 mM EDTA)). The DNA was subjected to constant current electrophoresis at 100 volts for 3 hours and data automatically analyzed using the 362 GENE SCANNER Fluorescent Fragment Analyzer. The results are shown in FIG. 3.

Panel A displays an electropherogram of the HUMHPRTB repeat in a patient with Turner's syndrome (45,XO), thus only a single peak is evident. Panel B displays an electropherogram of the HPRTB repeat in a patient with Triplo-X syndrome (47,XXX). Three peaks in approximately equal proportions are evident which is consistent with the triplozygous type diagnostic of trisomy DNA. Panel C displays an electropherogram of HPRTB STR amplified from a (48,XXXX) cell line, derived from a somatic tumor. It appears that each of the two chromosomes have been duplicated resulting in two peaks of equal intensity. Panel D displays an electropherogram of the HPRT STR from a tetrasomy (48,XXXX) patient. Three different peaks are evident, two minor and one major, indicating that one of the four alleles in present in double dosage. This is consistent with the DNA containing four copies of the X-linked repeat and points to a non-disjunction event during meiosis I since more than two distinct chromosomes are involved. Panel E displays an electropherogram of the X-linked STR in a patient with a pentasomy (49,XXXXX). The electropherogram contains four peaks-three minor and one major-corresponding to four different HPRTB alleles. The major peak indicates that one of the alleles is present in double dosage.

EXAMPLE 4

STR Dosage Allows Detection of Gene Level Aneuploidy in Lesch-Nyhan Syndrome

The HUMARA $[AGC]_n$ and HUMHPRTB $[AGAT]_n$ STRs from a sample taken from a Lesch-Nyhan patient were co-amplified using conditions described in Example 3, except that both STR markers were labeled with JOE (XHPRTF primer: JOE-5'-atg cca cag ata ata cac atc ccc-3'. PCR amplified DNA was automatically analyzed using a 363 GeneScanner (Applied Biosystems, Foster City). FIG. 4 compares results from the Lesch-Nyhan patient with male and female controls. Panel A is an electropherogram of the Lesch-Nyhan patient's DNA that contains a duplication in the vicinity of the HPRTB STR, which apparently gave rise to a higher concentration of this amplification product. Panel B displays data from a normal hemizygous male control, the ARA and HPRTB repeats being in approximately equal proportions. Panel C displays data from a heterozygous female control. Panel D displays data from a homozygous female control.

We claim:

1. A method for detecting the presence or absence of aneuploidy of a preselected human chromosome, the method comprising the steps of:
   a. simultaneously amplifying, using the polymerase chain reaction, one or more chromosome-specific short tandem repeats (STRs) each having a repeat unit of from 3 to 6 nucleotides to form an amplification product mixture comprising copies of the one or more chromosome-specific STRs in concentrations substantially proportional to their respective starting concentrations;
   b. separating the amplified chromosome-specific STRs from the amplified product mixture according to size;
   c. determining the relative concentrations of the amplified one or more chromosome-specific STRs, and
   d. correlating the relative concentration of each amplified STR with the presence or absence of aneuploidy of said preselected chromosome.

2. The method of claim 1 wherein step b includes separating by gel electrophoresis or capillary electrophoresis.

3. The method of claim 2 wherein said copies of said one or more chromosome-specific STRs are fluorescently labeled.

4. The method of claim 3 wherein said chromosome-specific STRs are selected from loci on a chromosome selected from the group consisting of chromosome 18, chromosome 21, chromosome X, and chromosome Y.

5. A method according to claim 1, the method further comprising the step of:
   e. counting the number of distinct amplification products from each STR and correlating the relative concentration of each STR amplification product with the presence or absence of aneuploidy of said preselected chromosome.

6. A method of claim 1, wherein the aneuploidy is a trisomy.

7. A method of claim 1, wherein more than one STR is amplified.

8. A method of claim 5, wherein the aneuploidy is a trisomy.

9. A method of claim 5, wherein more than one STR is amplified.

10. A method according to claim 1, wherein the STR is present on genetic material obtained from a fetal cell.

11. A method according to claim 1, wherein a plurality of different STRs are amplified.

12. A method according to claim 1, wherein the preselected chromosome is an autosome.

13. A method according to claim 1, wherein the preselected chromosome is a sex chromosome.

14. A method according to claim 11, wherein the presence or absence of plurality of preselected chromosomes is detected.

15. A method according to claim 1, wherein the step of determining the relative concentrations of the amplified chromosome-specific STRs comprises determining whether or not a specific-amplification product is present.

16. The method according to claim 1, wherein the preselected chromosome is the X chromosome.

17. The method according to claim 1, wherein the preselected chromosome is the Y chromosome.

18. The method according to claim 1, wherein the preselected chromosome is chromosome 18.

19. The method according to claim 1, wherein the preselected chromosome is chromosome 21.

20. The method of claim 5 wherein said step of separating includes separating by gel electrophoresis or capillary electrophoresis.

21. The method of claim 20 wherein said copies of said one or more chromosome-specific STRs are fluorescently labeled.

22. The method of claim 21, wherein said chromosome specific STRs are selected from loci on a chromosome selected from the group consisting of chromosome 18, chromosome 21, chromosome X, and chromosome Y.

23. A method according to claim 2, wherein the preselected chromosome is obtained from a fetal cell.

24. A method according to claim 5, wherein the STRs are present on genetic material obtained from a fetal cell.

25. A method according to claim 14, wherein the STRs are present on genetic material obtained from a fetal cell.

* * * * *